US012649713B2

(12) United States Patent
Schaefer et al.

(10) Patent No.: US 12,649,713 B2
(45) Date of Patent: Jun. 9, 2026

(54) ISOMERIZATION OF POLYUNSATURATED NON-AROMATIC COMPOUNDS

(71) Applicant: BASF SE, Ludwigshafen am Rhein (DE)

(72) Inventors: Bernd Schaefer, Ludwigshafen am Rhein (DE); Wolfgang Siegel, Ludwigshafen am Rhein (DE); Steffen Tschirschwitz, Ludwigshafen am Rhein (DE); Till Christian Brüggemann, Ludwigshafen am Rhein (DE); Marius Sorin Pulbere, Ludwigshafen am Rhein (DE); Florian Buchbender, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 942 days.

(21) Appl. No.: 17/616,911

(22) PCT Filed: May 28, 2020

(86) PCT No.: PCT/EP2020/064871
§ 371 (c)(1),
(2) Date: Dec. 6, 2021

(87) PCT Pub. No.: WO2020/245030
PCT Pub. Date: Dec. 10, 2020

(65) Prior Publication Data

US 2022/0315519 A1 Oct. 6, 2022

(30) Foreign Application Priority Data

Jun. 7, 2019 (EP) .................................... 19179061

(51) Int. Cl.
*C07C 67/293* (2006.01)

(52) U.S. Cl.
CPC ........ *C07C 67/293* (2013.01); *C07C 2601/16* (2017.05)

(58) Field of Classification Search
CPC ............ C07B 2200/09; C07B 2200/07; C07C 2601/16; C07C 403/12; C07C 403/20; C07C 67/293
See application file for complete search history.

(56) References Cited

U.S. PATENT DOCUMENTS

| | | | | |
|---|---|---|---|---|
| 3,838,029 A * | 9/1974 | Fisher et al. | C07C 403/12 204/157.67 |
| 4,026,778 A * | 5/1977 | Lalonde | C07C 403/08 204/157.67 |
| 6,489,438 B1 | 12/2002 | Erhardt et al. | |
| 2007/0215455 A1 | 9/2007 | Folkmann et al. | |

FOREIGN PATENT DOCUMENTS

| | | | |
|---|---|---|---|
| CN | 107935901 | * | 4/2018 |
| CN | 107935901 | A | 4/2018 |
| DE | 2210800 | B1 | 7/1973 |
| DE | 2548883 | A1 | 5/1976 |
| EP | 0742204 | A1 | 11/1996 |
| ES | 2378737 | T3 | 4/2012 |
| JP | 48-099145 | A | 12/1973 |
| JP | 2002-275101 | A | 9/2002 |
| JP | 2009-530317 | A | 8/2009 |

OTHER PUBLICATIONS

CN107935901 translation (Year: 2018).*
Hohman (LED Light Sources: A major Advance in Fluorescence Microscopy, 7 pages Dec. 2010) (Year: 2010).*
Santandrea et al. (Continuous Flow Science in an Undergraduate Teaching Laboratory: Photocatalytic Thiol-Ene Reaction Using Visible Light, J. Chem. Educ., 95, pp. 1073-1077, Published 2018) (Year: 2018).*
European Search Report for EP Patent Application No. 19179061.7, Issued on Dec. 16, 2019, 3 pages.
Gopal et al., "Semiconductor photoinduced isomerization of retinol acetate and retinol", Journal of Photochemistry and Photobiology A: Chemistry, vol. 74, Issue 1, Aug. 15, 1993, pp. 81-84.
International Preliminary Report on Patentability received for PCT Patent Application No. PCT/EP2020/064871, mailed on Dec. 16, 2021, 8 pages.
International Search Report and Written Opinion received for PCT Patent Application No. PCT/EP2020/064871, mailed on Aug. 18, 2020, 9 pages.
Roibu et al., "Design and characterization of visible-light LED sources for microstructured photoreactors", Reaction Chemistry & Engineering, vol. 3, No. 6, Oct. 9, 2018, pp. 849-865.

* cited by examiner

*Primary Examiner* — Amy C Bonaparte
*Assistant Examiner* — Blaine G Doletski
(74) *Attorney, Agent, or Firm* — Faegre Drinker Biddle & Reath LLP

(57) ABSTRACT

The invention relates to an improved process for isomerizing polyunsaturated non-aromatic compounds including acyclic conjugated polyenes and alicyclic conjugated polyenes. In particular it relates to an improved and safe process for forming a 11-E retinoid compounds in high yield by expending as few energy as possible and with avoiding at most possible side products or product mixtures. This is achieved by feeding at least one of retinoid compounds of formula 2 to 5, or at least one of retinoid compounds of formula 2 to 5 and retinoid compound of formula 1, an organic solvent and a photosensitizer into a reaction device and irradiating the thus obtained reaction mixture with visible monochromatic light, at least 90% of the power of said monochromatic light and at most 100% of said power being emitted in the range from 460 nm to 580 nm.

22 Claims, 3 Drawing Sheets

ISOMERIZATION OF POLYUNSATURATED NON-AROMATIC COMPOUNDS

CROSS-REFERENCE TO RELATED APPLICATIONS

This application is a national stage application (under 35 U.S.C. § 371) of PCT/EP2020/064871, filed May 28, 2020, which claims benefit of European Application No. 19179061.7, filed Jun. 7, 2019, both of which are incorporated herein by reference in their entirety.

The invention relates to an improved process for isomerizing polyunsaturated non-aromatic compounds including acyclic conjugated polyenes and alicyclic conjugated polyenes. In particular it relates to an improved and safe process for forming all-E retinoid compounds in high yield by expending as few energy as possible and with avoiding at most possible side products or product mixtures.

Figure 1:
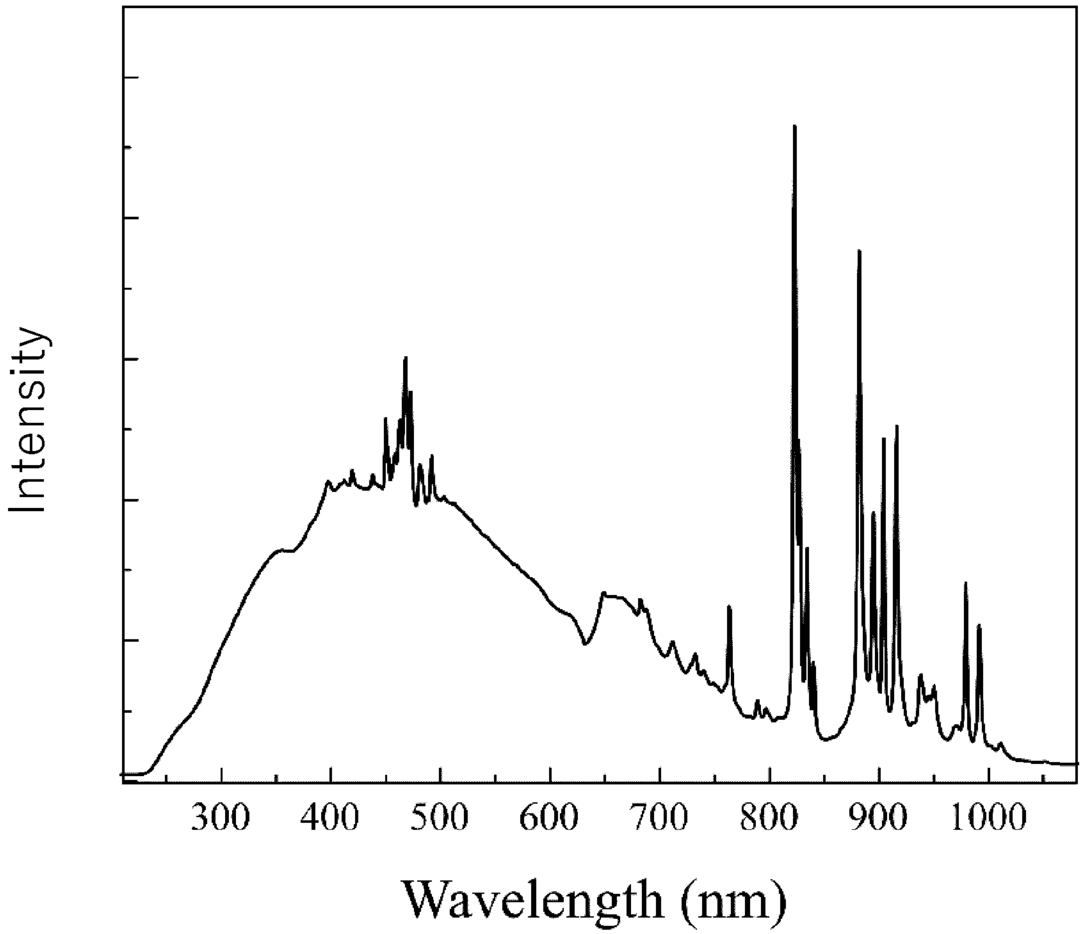

DE 25 48 883 describes a process for photo-isomerizing vitamin A compounds of different conformation into their all-E entities by means of a 150 W xenon gas discharge lamp or xenon arc lamp (cf. examples 1 and 2). Such xenon arc lamp provides an emission spectrum or output profile as shown in FIG. 1. One observes a considerable peak or mountain extending from 240 nm to 1000 nm, which is to say extensive lighting takes place even in the range from 240 nm to 400 nm. Such lighting (UV-light) can cause any kind of isomerization even into undesired compounds like 9Z-retinoids ('883, page 5), which by further irradiation is hard to be converted into an all-E retinoid compound synonymous to an all-trans retinoid compound. In all embodiments, mixtures of isomers (e.g. 60-90% all-E, 10-30% 9Z an 5% 13Z retinol acetate) are obtained, independently of the composition of the starting material. This is to say a starting material already containing an excess of all-E retinoid compound reduces said all-E excess due to photoirradiation with the xenon arc lamp. Furthermore, said highly energetic radiation, mostly in the UV-range is suitable to irreversibly bleach or destroy polyene compounds like vitamin A. Another drawback of UV light is dimer formation and solvolysis (cf. DE 2 210 800 column 1, line 66 till column 2, line 4).

'883 tolerates such inconvenience as it specifically claims irradiation to take place between 240 nm and 450 nm. Any protection means such as photosensitizers, which would at least partially prevent damages caused by light of this wavelengths on the vitamin A compounds, are explicitly excluded (cf. claim 1). Likewise, filtering means are proposed only for preventing light below 240 nm to penetrate into the reaction chamber (cf. page 7, para. 3). Thus, highly energetic UV-light commencing at 240 nm still penetrating the interior of the reaction device, can deliberately interact with vitamin A compounds and spoil them.

According to the output profile in FIG. 1, xenon gas discharge lamps or xenon arc lamps show a spectrum with strong emission extending almost over the whole range from far UV-light till infrared light. Indeed, a huge amount of energy consumed by a xenon gas discharge tube or xenon gas discharge lamp is released in form of heat (~64%), thus making such light source not very environmentally friendly. Furthermore, a lot of electric energy applied to generate lighting by xenon gas discharge will be dissipated at wavelengths having no effect onto isomerizing cis-vitamin A compounds. Exploiting only a small portion of the light spectrum generated by a xenon arc lamp or xenon gas discharge lamp would mean, especially if used on industrial scale, not only to waste much of precious electrical energy but also to provide costly means for discharging the excess of heat, viz. infrared radiation generated from such lamp.

A further drawback of using xenon gas discharge lamps is their high price. Their handling is neither easy nor safe since during operation high temperatures, temperature gradients and pressures are generated in the lamp interior. Such operation conditions easily lead to severe burn injuries upon contact or to cuts caused by explosion due to mechanical shocks the lamp may be exposed to during operation. Consequently, such lamps can only be used by especially trained staff, which is required to use protective clothing. Most xenon discharge lamps require cooling devices and explosion-proof housing in order to be operated safely. This is cumbersome and expensive.

Yet another drawback of the '883 paper is the use of a base, viz. of tripropylamine in the photo-isomerizing process. Using bases with polyunsaturated compounds can lead to further reactions especially under the lighting conditions given in this publication. Such bases have to be removed.

EP 0 742 204 A1 discloses a process for transforming 11-cis, 13-cis retinoic acid into 13-cis retinoic acid by irradiating it at a wavelength of 400 to 700 nm emerging from the 8 W Hitachi lamp F875/CW in a solvent mixture containing 7 parts of acetonitrile having a triple bond and 3 parts of methylene chloride. The formation of all-trans retinoic acid is not disclosed.

In V. Raj Gopal et al. J. Photochem. Photobiol. A: Chem. 74 (1993), 81-84 retinol and retinol acetate solutions are suspended with the semiconductors CdS, CdSe and irradiated with a 450 W medium pressure mercury lamp. $NaNO_2$— and $K_2Cr_2O_7$—$CuSO_4$ are used as filtering means to remove wavelengths below 500 nm and below 400 nm. Said arrangement is sensitive to oxygen acting as efficient quencher. The photoisomerization process is selectively restricted to trisubstituted double bonds of retinoids (13-cis and 9-cis). The amount of all trans isomer decreases with time (cf. FIG. 1, 2) and there is a preference for forming the 13-cis isomer. No method increasing the amount of all trans retinoids is given.

Figure 2:
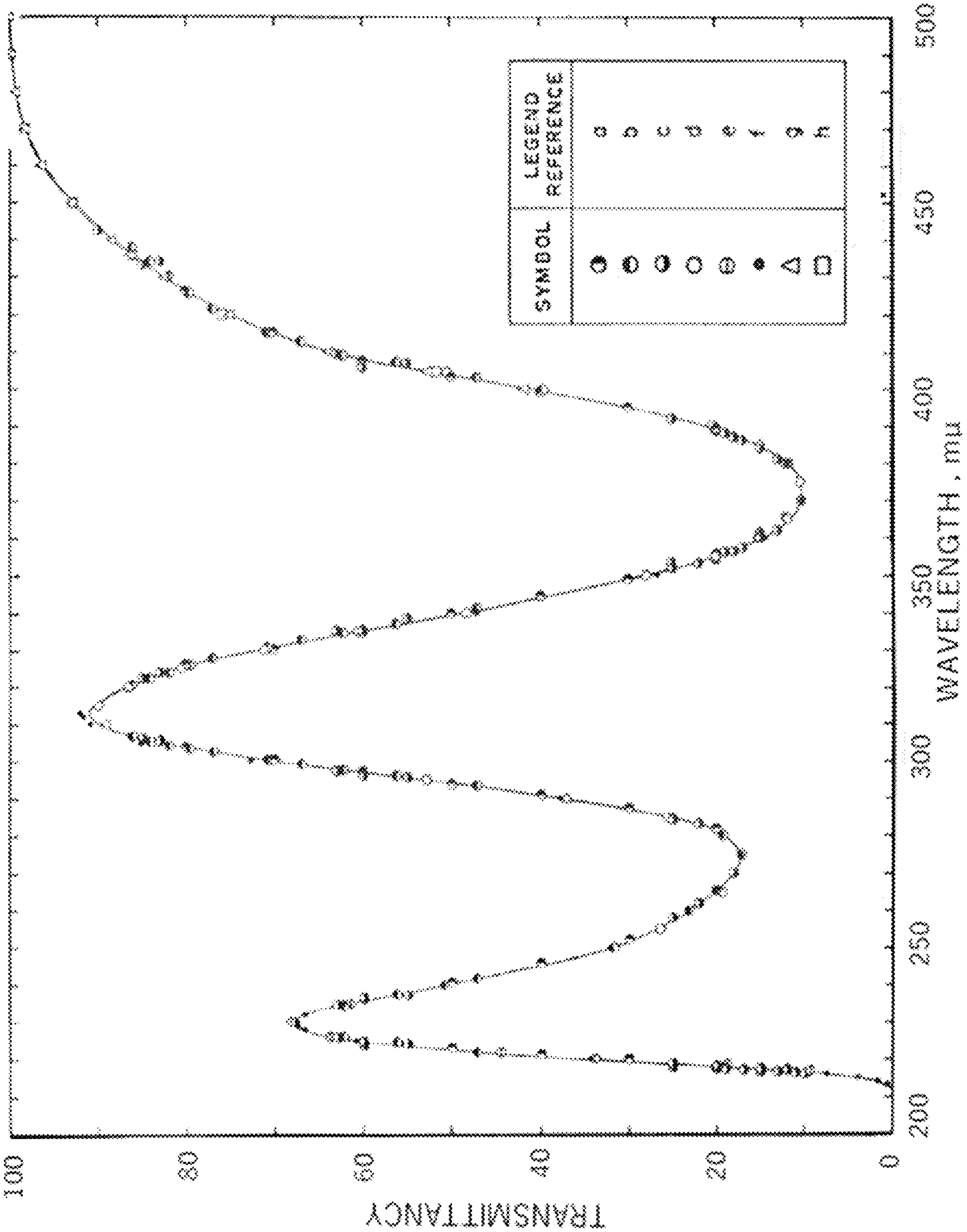

DE 22 10 800 teaches to isomerize mixtures of vitamin A isomers by means of a thallium iodide doped high pressure mercury vapor lamp in the presence of a photosensitizer (cf. i.a. example 1). Damaging short wave light is partially removed by means of a potassium chromate solution serving as filtering means (cf. example 1). However, said chromate solution still shows a strong transmittance between 290 nm to 360 nm as can be seen in FIG. 2. This is to say that only UV-light below 290 nm is successfully removed by the filtering means, still leaving a UV light portion above 290 nm to irradiate the sample to be reacted (cf. radiation flux generated by a thallium iodide doped high pressure mercury vapor lamp of type TQ 150 Z2 inter alia at wavelengths of 313, 322, 334, 352 and 366 nm as given in Table A below under 1).

Working with the thallium iodide-doted high-pressure mercury vapor lamp under the conditions given in example 1 of the '800 publication gives already access to eliminate to some extent detrimental high energetic light and to avoid side reactions more effectively compared to the '883 paper. However, using a high-pressure mercury lamp still suffers from the following drawbacks, which make an industrial process expensive and sophisticated and provides highly toxic waste, when the high-pressure mercury vapor lamp breaks or runs out of service.

1. Mercury lamps emit light energy scattered over numerous lines in the Hg spectrum. The spectrum ranges from about 230 to 600 nm. Typical signals of a thallium iodide doped high pressure mercury vapor lamp of type TQ 150 Z2 are as shown in Table A below:

TABLE A

| | | | | | | | | | |
|---|---|---|---|---|---|---|---|---|---|
| Wavelength [nm]: | 238 | 248 | 254 | 270 | 275 | 289 | 302 | 313 | 322 |
| Radiation flux [W] | 0.5 | 0.2 | 2.1 | 1.4 | 2.6 | 3.3 | 0.5 | 1.8 | 1.0 |
| Wavelength [nm]: | 334 | 352 | 366 | 378 | 405 | 436 | 536 | 546 | 577 |
| Radiation flux [W] | 0.4 | 6.3 | 3.6 | 3.9 | 1.1 | 2.3 | 13.5 | 2.7 | 1.7 |

However, only the energy of a distinct number of these lines can be used to initiate a chemical reaction, the remaining light to some extent being emitted without any use into the surrounding and to some extent being detrimental to all-E retinoid compounds. Said light however, is hazardous for those running the apparatus, said apparatus therefore has to be consciously and costly shielded or wrapped.

2. The light yield (light output/electric power input) in commercial doped mercury lamps (e.g. TQ 150 Z2) is only in the range of 5-10%, based on the radiant flux applied for the photoreaction. 90-95% of the electric power are transformed into heat and emitted on the bright side of the lamp, which makes a sophisticated cooling system mandatory. The loss of electric energy is considerable.
3. Even in appropriately doped mercury lamps, optical filters must be applied, in order to prevent degradation of the vitamin A compounds in particular retinol esters by the amount of UV light (<400 nm) still emitted. The state-of-the-art solution are potassium chromate filters with their drawbacks as indicated supra. Potassium chromate is a toxic, environmental hazardous, mutagenic and cancerogenic salt.
4. The high pressure mercury lamp mediated isomerization of 11Z vitamin A compounds (e.g. retinol esters) to all-E vitamin A compounds (e.g. retinol esters) is accompanied with the formation of various other Z isomers, e.g. 9Z retinol esters, 13Z retinol esters, and 9Z,11Z retinol esters, all of them are not desired and thus reduce the overall yield of all-E retinoid compound.
5. Up to now, in most industrial photochemical processes 5-60 kW mercury lamps were applied. However, for environmental protection reasons and in order to no longer expose the lamp producer to hazardous working conditions, the manufacturing of mercury lamps might fade-out soon, triggered by the UN Mercury regulation (Minamata Convention on Mercury, EuP directive 2005/32EG). Also for this reason, there is a need to improve isomerization reaction conditions of vitamin A compounds.

According to the teaching of the prior art, light for isomerizing vitamin A always comprises a UV-light portion. One even gets the impression, that UV light up to 400 nm is mandatory for properly realizing an isomerization of vitamin A compounds, and one has to tolerate the detrimental effects said same UV radiation has on vitamin A compounds.

It is an object of the invention to overcome the previously mentioned manifold drawbacks and to devise an improved process for obtaining an all-E polyunsaturated non-aromatic compound including acyclic conjugated all-E polyenes and alicyclic conjugated all-E polyenes, in particular an all-E retinoid compound of formula 1. Said process shall at most possible and in a highly preferred way entirely avoid the damages on polyunsaturated compounds caused by UV-irradiation. It shall be cheap, fast and provide high selectivities for and high yields of all-E polyunsaturated non-aromatic compound, in particular all-E retinoid compound of formula 1. Elaborate cooling-, shielding- and explosion protection means shall be avoided by the new process and it shall be safe and straightforward. Filtering means both in form of a solution or a solid means shall be avoided. Complicated reaction mixtures and their tedious work-up are to be reduced to the utmost extent possible. It is also an object of the inventive process compared to the prior art, to safe energy with respect to the amount of all-E polyunsaturated non-aromatic compound, in particular of all-E retinoid compound of formula 1 produced. The amount of energy required for obtaining such all-E polyunsaturated entity, in particular of such all-E retinoid compound of formula 1, shall be adjustable with respect to reaction conditions. Easy up- and downscaling of the inventive process shall be possible without far-reaching changes in the reaction setup.

The inventive object is achieved by a process for obtaining an all-E retinoid compound or a mixture of all-E retinoid compounds of formula 1

1

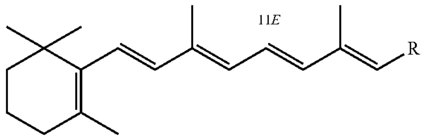

with R being selected from the group of moieties consisting of $CH_2$—OH, CHO, $CH_2$—$OR^2$, COOH, $COOR^3$;

with $R^2$ being (C═0)-alkyl;

with $R^3$ being alkyl;

with alkyl being selected from the group consisting of methyl, ethyl, propyl, isopropyl, butyl, 2-butyl, sec-butyl, isobutyl, tert.-butyl;

comprising the reaction steps:

feeding a retinoid compound of formula 2

2

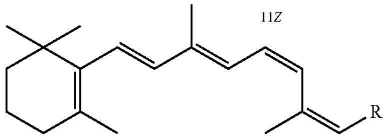

or a retinoid compound of formula 3

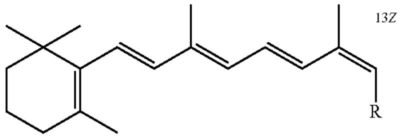

3 or a retinoid compound of formula 4

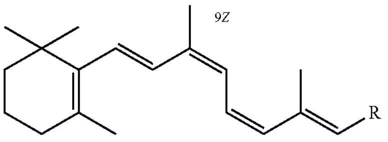

4 or a retinoid compound of formula 5

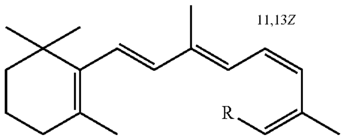

5 or a mixture of at least two of retinoid compounds 2 to 5,
or a mixture of at least one of retinoid compounds 2 to 5 and retinoid compound of formula 1,
an organic solvent and a photosensitizer into a reaction device,
irradiating the thus obtained reaction mixture by means of a filter-free, electroluminescent lighting device emitting monochromatic light, at least 90% of the power of said monochromatic light and at most 100% of said power being emitted in the range from 460 nm to 580 nm.

It was surprising to observe high yields of all-E polyunsaturated non-aromatic compounds including acyclic conjugated all-E polyenes and alicyclic conjugated all-E polyenes, and in particular of all-E retinoid compounds of formula 1, by almost exclusively or exclusively using visible light in the range as claimed. This is in contrast to the prior art supposing UV-light to be mandatory for realizing a Z-E isomerization within a distinct retinoid compound, said retinoid compound not being bound to any supporting means like e.g. a protein. Said high yields are even be obtained upon spending only half of the electric energy as used with a high-pressure mercury vapor lamp. Albeit said low consumption of electric energy, selectivity towards all-E polyunsaturated non-aromatic compounds, particularly towards all-E retinoid compounds of formula 1 is higher compared to using a high-pressure mercury vapor lamp of the prior art. Bleaching or spoiling of polyunsaturated compounds was not observed neither in the starting material nor in the product. Raw mixtures immediately after irradiation are much less complex compared to those obtained with the methods of the prior art. The new inventive process does not require any enzyme nor any biochemical reaction step. The risk of skin and vision impairment of individuals realizing the inventive process is largely reduced, in some embodiments with low energy impact even completely avoided, since one employs almost totally visible light or only visible light.

An all-E retinoid compound of the invention is any compound of formula 1 with R being selected from the group consisting of $CH_2$—OH, CHO, $CH_2$—O—C(═O)—$CH_3$, $CH_2$—O—C(═O)—$CH_2$—$CH_3$, $CH_2$—O—C(═O)—$CH_2$—$CH_2$—$CH_3$, $CH_2$—O—C(═O)—CH—$(CH_3)_2$, $CH_2$—O—C(═O)—$CH_2$—$CH_2$—$CH_2$—$CH_3$, $CH_2$—O—C(═O)—CH—$(CH_3)$—$CH_2$—$CH_3$, $CH_2$—O—C(═O)—$CH_2$—$CH(CH_3)_2$, $CH_2$—O—C(═O)$C(CH_3)_3$, COOH, $COOCH_3$, COO—$CH_2$—$CH_3$, COO—$CH_2$—$CH_2$—$CH_3$, COO—CH—$(CH_3)_2$, COO—$CH_2$—$CH_2$—$CH_2$—$CH_3$, COO—CH—$(CH_3)$—$CH_2$—$CH_3$, COO—$CH_2$—$CH(CH_3)_2$, COO—$C(CH_3)_3$, which is to say all-E retinol, all-E retinal, all-E retinyl acetate, all-E retinyl propionate, all-E retinyl butyrate, all-E retinyl isobutyrate, all-E retinyl pentanoate, all-E retinyl sec-pentanoate, all-E retinyl iso-pentanoate, all-E retinyl tert.-pentanoate, all-E retinoic acid, all-E retinoic acid methyl ester, all-E retinoic acid ethyl ester, all-E retinoic acid propyl ester, all-E retinoic acid isopropyl ester, all-E retinoic acid butyl ester, all-E retinoic acid 2-butyl ester, all-E retinoic acid sec butyl ester, all-E retinoic acid isobutyl ester, all-E retinoic acid tert.-butyl ester.

Cis retinoid compounds of formulas 2, 3, 4 and 5 have the same molecular formulas and the same molecular weights as the respective compounds given under formula 1. However, their stereochemistry varies from these of formula 1. Retinoid compound 2 has an 11Z-conformation, retinoid compound 3 has a 13Z conformation, retinoid compound 4 has a 9Z conformation and retinoid compound 5 has an 11,13Z conformation.

In one embodiment of the invention one uses at least one of the retinoid compounds of formula 2, formula 3, formula 4 or formula 5 as raw material or starting material. In a further embodiment one employs at least one of the retinoid compounds of formula 2, formula 3, formula 4 or formula 5 combined with an all-E retinoid compound of formula 1 as raw material or starting material. This is to say, that not only distinct cis-isomers of formula 2 to 5 or mixtures thereof are used as raw material, but also mixtures comprising the product of formula 1 in addition to at least one of the retinoid compounds of formula 2 to 5. The inventive process thus is adapted to be used for pure raw material as well as for mixtures comprising inter alia raw material and product of formula 1.

An important feature of the inventive process is an organic solvent into which one solubilizes at least one of the retinoid compounds 2 to 5 or a mixture as previously indicated.

Without using such solvent, photo-isomerization would also take place, however, work-up at the end of the photo-isomerization would be more tedious.

An organic solvent according to the invention is each solvent, which does not interfere with the reaction course of the inventive process, viz, which does not interact with the light applied and the retinoid compounds of formula 1 to 5. In particular an organic solvent is understood to be at least one compound being selected from the group consisting of C1-C6 alcohols; C5-C10 hydrocarbons; C1-C4 halogenhydrocarbons of the formula $C_xH_mCl_n$ with x representing the number of carbon atoms, m representing the number of hydrogen atoms, n representing the number of chlorine atoms and m+n=2x+2; C2-C4 hydrocarbons of the formula $C_yH_mCl_n$ with y representing the number of carbon atoms, m representing the number of hydrogen atoms, n representing the number of chlorine atoms and m+n=2y; carboxylic esters of the formula L1-COO-L2 with L1 being selected from the group consisting of methyl, ethyl, propyl, isopropyl and L2 being selected from the group consisting of methyl, ethyl, propyl, isopropyl, n-butyl, 2-butyl, sec-butyl, tert.-butyl; ethers of the formula L2O-L2 with L2 having the meaning as previously defined; tetrahydrofuran; dioxane; ketones of the formula L3-(C═O)-L3 with L3 being selected from the group consisting of methyl, ethyl, propyl, isopropyl, n-butyl, 2-butyl, sec-butyl, tert.-butyl, n-pentyl, 2-pentyl, sec.-pentyl, 3-pentyl or amyl, 2-methyl butyl; dimethylformamide; N-methyl-2-pyrrolidone; dimethyl sulfoxide; benzene; toluene; xylene; chlorobenzene.

The group of C1-C6 alcohols consists of methanol, ethanol, n-propanol, isopropanol, n-butanol, sec-butanol, isobutanol, tert.-butanol, n-pentanol, 2-pentanol, 3-pentanol, 3-methylbutan-1-ol or iso-pentanol, tert.-pentanol or 2-methyl-butan-2-ol, cyclohexanol.

C5-C10 hydrocarbons are understood to be hydrocarbons having at least 5 carbon atoms and at most 10 carbon atoms which are bound to hydrogen atoms only. They are selected from the group of n-pentane, isopentane and all other isomeric forms of pentane, n-hexane and all other isomeric forms of hexane, n-heptane and all other isomeric forms of heptane, n-octane and all other isomeric forms of octane, 2-methylpentane, 2,2,3-trimethylpentane or isooctane, cyclopentane, cyclohexane, cyclooctane, petroleum ether, white spirit, methyl cyclohexane, nonane in all its isomeric forms, decane in all its isomeric forms.

An important aspect of the inventive process is the use of a photosensitizer. Said photosensitizer is understood to at least partially absorb radiation between 460 and 580 nm and to transform it into energy being capable to excite electrons in cis-double bonds of retinoid compounds 2 to 5. Once excited said cis double bonds are capable to dissociate and to rearrange into a trans or E orientation. In the prior art said isomerization always was achieved by means of UV-light below 400 nm sometimes combined with visible and eventually thermal radiation. However, no process nor device was proposed up to now, exclusively or quasi-exclusively using visible light, in particular monochromatic light as defined infra, for isomerizing at least one of retinoid compounds 2 to 5 to obtain retinoid compound of formula 1 in high yield.

The term reaction mixture within the inventive process is understood to comprise at least one of retinoid compounds 2 to 5, optionally retinoid compound of formula 1, the organic solvent as defined and at least one photosensitizer.

Monochromatic light as understood within this disclosure is all radiation at least 90% of its power and at most 100% thereof being emitted in the range from 460 nm to 580 nm. The power of minor components of the monochromatic light being outside the given wavelength range at most amounts up to 10% depending on the filter-free electroluminescent lighting device employed, the nature and quantity of the photosensitizer and the organic solvent. However, the great majority of embodiments of monochromatic light only contains small amounts of light portions beyond 460 nm to 580 nm. In one embodiment monochromatic light is understood to be an entity, at least 95% of the power of said monochromatic light and at most 100% of said power being emitted in the range from 460 nm to 580 nm. In yet another embodiment monochromatic light means, at least 98% and further preferred at least 99% of the power of said monochromatic light and at most 100% of said power being emitted in the range from 460 nm to 580 nm. The amount of the monochromatic light is expressed in power since by doing so one is not urged to otherwise define the permissible amount of light in lumen lm or Wh or candela cd above and below the claimed wavelength range. Said amount, when not expressed in power, would vary as a function of the wavelength considered. In yet a further specified embodiment, monochromatic light, as understood within this disclosure, is all radiation at least 90% of its power and at most 100% thereof being emitted in the range from 460 nm to 580 nm and its monomodal emission spectrum exhibiting a half-width of +/−10 to +/−30 nm in relation to the wavelength of the emission maximum. Said defined halfwidth gives a highly structured lighting signal, which results in an improved yield of retinoid compound of formula 1.

A filter-free electroluminescent lighting device within this disclosure is any electroluminescent device emitting light, which can be operated for a deliberately chosen time period merely by turning it off and on, and which does not comprise a filtering means. A filtering means can be a layer, a chemical compound or product applied onto the lighting device. A filtering means can also be a compound, which is immersed or solubilized in a solvent circulating, pumped or floating around the lighting device and adapted to absorb light in a distinct range but not to transfer energy emerging from said absorbed light onto one of retinoid compounds 1 to 5. The electroluminescent lighting device is required not to operate by means of any kind of chemically induced lighting like gas ionization or by means of heating. The filter-free electroluminescent lighting device is understood to provide light (photons) emerging from electrons supplementing holes or gaps in an electron-poor material with emission of electromagnetic radiation preferably in the form of visible light. Said filter-free electroluminescent lighting device is selected from the group of light emitting electrochemical cells, electroluminescent wires, field-induced electroluminescent polymers, light emitting diodes, organic light emitting diodes, polymer light emitting diodes, active-matrix organic light-emitting diodes (AMOLED's), electroluminescent films especially based on inorganic luminescent materials, semiconductor lasers, diode lasers, chemical lasers, dye lasers, free-electron lasers, gas dynamic lasers, gas lasers, ion lasers, laser flashlights, metal-vapor lasers, monolinear optics quantum well lasers, ruby lasers, solid-state lasers. Preferably, said filter-free electroluminescent lighting device is selected from the group of light emitting electrochemical cells, electroluminescent wires, field-induced electroluminescent polymers, light emitting diodes, organic light emitting diodes, polymer light emitting diodes, active-matrix organic light-emitting diodes (AMOLED's), electroluminescent films especially based on inorganic luminescent materials, In a further elaborated embodiment of the inventive process at least 90% of the power of said monochromatic light and at most 100% of said power being emitted in the range from 501 nm to 550 nm. Working at this somewhat smaller wavelength range still provides good conversion rates into and high yields of all-E polyunsaturated non-aromatic compounds including acyclic conjugated all-E polyenes and alicyclic conjugated all-E polyenes, and in particular of all-E retinoid compounds of formula 1, however, by means of a narrower wavelength spectrum thus expending less power and energy. Side reactions like e.g. isomerization into undesired compounds are even further suppressed or preferably completely avoided at this wavelength range. Narrowing of the wavelength range within the filter-free, electroluminescent lighting device is achieved by selectively controlling distinct electronic parts within said device.

Another important feature of the inventive process is to carefully control the amount of energy to be introduced into the reaction mixture. This is achieved by selecting the monochromatic light such that the electric energy consumed by the lighting device for obtaining 1 kg of retinoid compound of formula 1 does not exceed 800 Wh. When doing so, damaging of compounds in the reaction mixture is largely reduced and preferably even completely avoided. Likewise, the formation of undesired isomers of retinoid compound of formula 1. This is crucial since especially formation of undesired retinoid compound 4 is the harder to reverse the longer the inventive process progresses. After a certain reaction time one is no longer in a position to get rid of retinoid compounds 3 and 4 formed during the course of the reaction. With other words, it is mandatory to choose reaction conditions such that the amount of retinoid compounds 3 and 4, when present in the reaction mixture, decreases already in the beginning of the inventive process and de novo formation thereof shall not take place. One parameter to be considered for this is the amount of energy brought into the reaction mixture.

This control of energy is hardly or only roughly possible when using any kind of mercury vapor lamp or a xenon arc lamp respectively xenon gas discharge lamp. These lamps have broad emission spectra exhibiting a multitude of peaks of different energy. Furthermore, such lamps change their overall intensity of peaks with their hours of use. Energy delivery decreases with using time and one has to determine or to estimate it on a regular basis and to adjust the amount of energy delivered. This is cumbersome and time consuming and does not qualify for an economic industrial process.

The inventive process gives varying yields of all-E polyunsaturated compound, depending on the residue R chosen in the all-E polyunsaturated non-aromatic compounds including acyclic conjugated all-E polyenes and alicyclic conjugated all-E polyenes. In particular, this holds for the retinoid compounds 1 through 5. High yields of all-E retinoid compound of formula 1 in definite and well structured or crystallized form are obtained when the residue R is $CH_2$—O—(C═O)-alkyl with alkyl being selected from the group of methyl, ethyl. Complicated reaction mixtures, difficult to separate do not occur. This is to be at least partially attributed to the distinct solubility and precipitating or crystallizing ability of the respective cis retinoid esters 2 to 5 with R as previously defined compared to the respective all-E retinoid esters or all-trans retinoid esters with R as previously defined. All-E-retinoid esters with R being $CH_2$—O—(C═O)—$CH_3$ or $CH_2$—O—(C═O)—$CH_2$—$CH_3$ in various solvents or solvent mixtures tend to precipitate whereas their corresponding cis-isomers of formula 2 to 5 do not.

It was already stated earlier, that it is feasible but tough to isomerize retinoid compounds of formula 3 and 4 into their corresponding all-E retinoid compound of formula 1. Likely, this also holds for cis polyunsaturated non-aromatic compounds including acyclic conjugated cis polyenes and alicyclic conjugated cis polyenes, with these cis-polyunsaturated compounds having at least one cis-double bond. An extended version of the inventive process addresses this issue and defines that the weight portion of the sum of retinoid compound of formula 1 and of formula 2 prior to irradiation amounts to at least 80 w % of the retinoid compounds present in the reaction mixture, said retinoid compounds being selected from the group of retinoid compound of formula 1, retinoid compound of formula 2, retinoid compound of formula 3, retinoid compound of 4 and retinoid compound of formula 5. Preferably, the weight portion of the sum of retinoid compound of formula 1 and of formula 2 prior to irradiation amounts to at least 82 w % of the retinoid compounds present in the reaction mixture, more preferably to at least 85 w %, further preferred to at least 90 w % and mostly preferred to at least 92 w %, said retinoid compounds being selected from the group of retinoid compound of formula 1, retinoid compound of formula 2, retinoid compound of formula 3, retinoid compound of formula 4 and retinoid compound of formula 5. When using a mixture of retinoid compounds 1 to 5 with the amounts as indicated supra, the inventive process is rather straightforward. Complicated heavy to separate mixtures are avoided as well as high amounts of the undesired retinoid compound of formula 4. Crystallization of retinoid compound of formula 1 takes place immediately in a selection of solvents, which is harder to be achieved otherwise.

Another topic of making the inventive process fast and thus cost-saving and to avoid elaborated work-up mandatory for complicated reaction mixtures, is to work in an appropriate organic solvent. An appropriate organic solvent shall have the ability to at least partially discriminate between all-E retinoid compound of formula 1 on one hand and the retinoid compounds of formula 2 to 5 as well as the photosensitizer on the other hand, for instance by making reference to their different solubility or repartition behavior in said solvent. Such object is achieved by a further embodiment of the invention with the organic solvent being selected from at least one representative of the group of C1-C6-alcohols, preferably from methanol and ethanol or a mixture thereof. Such C1-C6 alcohols in particular methanol and ethanol respectively more readily solubilize retinoid compounds of formula 2 to 5 and they only scarcely to not at all solubilize retinoid compounds of formula 1. The term C1-C6-alcohols has the meaning as indicated above in this disclosure.

The previously mentioned embodiment avoids highly complex reaction mixtures but generally requires longer reaction times, which increases the risk of formation of retinoid compounds 2 to 5. It can also at least partially lead to oiling-out of retinoid compound of formula 1 instead of its crystallization. Oiling-out compound 1 may partially be associated with at least one of oiling-out compounds of formula 2 to 5. This is avoided, if one uses in yet a further extension of the inventive process as organic solvent a mixture of at least one representative of the group of C1-C6-alcohols and at least one C5-C10 hydrocarbon. C1-C6-alcohols and C5-C10 hydrocarbon have the meaning as indicated supra. C1-C6-alcohols per se contain water to a somewhat more or less pronounced extent. This can lead to interphases or not really proper separation between the alcohol and the water which has consequences onto the repartition of the different components of the reaction mixture. Supplementing the C1-C6-alcohols with a C5-C10 hydrocarbon ab initio makes the alcohol phase more hydrophobic thus leading to a better separation of all-E retinoid compound of formula 1 from retinoid compounds 2 to 5 and/or from the photosensitizer. Oiling-out of retinoid compounds 1 to 5 can be reduced by said measure, making isolation of compound 1 faster and simpler.

C1-C6-alcohols and C5-C10 hydrocarbon give two distinct phases when mixed in equal amounts. Under these conditions the inventive process can be realized successfully, when the reaction mixture is vigorously stirred. This embodiment has the advantage of being able to separate different kinds of compounds of the reaction mixture as a function of their overall polarity merely by stopping the stirring means. However, this advantage makes crystallization of all-E retinoid compound of formula 1 more sophisticated, since all compounds of the reaction mixture will be continuously mixed during stirring of the reaction mixture, and once stirring is stopped, they will partition into the respective phase according to their respective polarity. A largely reduced but very small oiling out of retinoid compound of formula 1 instead of its crystallization can occur, provided one works with highly concentrated reaction mixtures. This even further simplifies the isolation of compound 1 from the reaction mixture.

Surprisingly still better crystallization pattern in higher yield and shorter reaction time of all-E retinoid compound of formula 1, however, was observed when in a yet further developed embodiment of the invention, the mixture of at least one representative of the group of C1-C6-alcohols and at least one C5-C10 hydrocarbon is selected such that it forms a uniform phase. A uniform phase means that the two solvents mix between each other in such a way, that they cannot be identified as two separated entities. This is to say, that the amount of C5-C10 hydrocarbon in the organic solvent is minor and not allowed to exceed a certain threshold. Oiling out of all-E retinoid compound of formula 1 was not observed. Instead crystallization takes place during irradiation, the amount of solubilized all-E retinoid compound of formula 1 decreases and new solubilized all-E retinoid compound of formula 1 occurs as formed from the irradiation process. Said new all-E retinoid compound of formula 1 once saturated in solution also crystallizes and so on. This feature strongly promotes quick forming of all-E retinoid compound of formula 1.

Further trials have shown to give timely optimized crystallization of highly homogeneous crystals of all-E retinoid compound of formula 1, when the mixture of at least one representative of the group of C1-C6-alcohols and at least one C5-C10 hydrocarbon comprises between 0.1 and 12 w % of a hydrocarbon, further preferred between 1 and 12 w % of heptane including 10 w % and mostly preferred between 1 and 5 w % of heptane. Formation of interphases and partial oiling out of all-E retinoid compound of formula 1 were not observed. Due to timely crystallization, long reaction times can be avoided thus completely preventing the formation of undesired retinoid compounds of formula 4.

One beneficial feature of the invention is to avoid UV-irradiation in the inventive process. It was observed, even when only using visible light as radiation for the photochemical reaction of the inventive process, that considerable increase of reaction rate takes place, when using at least one particular photosensitizer. A further embodiment of the invention thus discloses the inventive photosensitizer to be selected from at least one compound of the group consisting of fluorescein, eosin, rose bengal, erythrosine, cobalt-tetraphenylporphyrin, zinc-tetraphenylporphyrin, rhodamine B, basacryl brilliant red, iodine.

A further important embodiment of the inventive process discloses the filter-free, electroluminescent lighting device to comprise a semiconductor material. Said semiconductor material satisfies several objects of the invention. It provides radiation of a selected wavelength or wavelength range outside the UV range. Damaging of polyunsaturated non-aromatic compounds, including acyclic conjugated all-E polyenes and alicyclic conjugated all-E polyenes, and in particular of retinoid compounds of formula 1 to 5 thus can be largely reduced, preferably even completely avoided. One therefore does not require any shielding or filtering of hazardous or detrimental light not being within the desired wavelength range. Likewise, elaborate cooling or explosion protection is not required, since a lighting device comprising a semiconductor is not prone to explode nor to emit a huge amount of heat. Semiconductor materials in general only consume comparable low amounts of electric energy and their ability of debiting light can be easily controlled or adjusted, either by adjusting current and voltage or by varying the amount of semiconductor material employed. Time of exposure of the reaction mixture to light emitted from the semiconductor material can be easily and repeatedly controlled simply by switching on or off the current passing through said material of the electroluminescent lighting device. Said procedure is not possible with xenon arc lamps or high-pressure mercury lamps, since switching them on needs time and repeated switching dramatically reduces their life time. The amount of energy spent on generating photochemical irrelevant radiation is considerably reduced, since the emission spectrum of semiconductor materials only has a defined band width, preferably adapted to the radiation required to trigger the inventive isomerization process. Said semiconductor material is selected from at least one compound of the group consisting of silicon, diamond, germanium, α-tin, α-sulfur, selenium, tellurium, BN, BP, BAs, $B_{12}As_2$, AlN, AlP, AlAs, AlGaN, AlGaP, $Al_xGa_{1-x}As$, AlGaAsN, AlGaAsP, AlGaInP, $Al_xIn_{1-x}As$, AlInAsP, AlSb, $Al_xIn_{1-x}Sb$, GaN, GaAsN, GaP, GaAs, GaAsP, GaAsSb, GaAsSbN, GaAsSbN, GaInAsSbP, GaMnAs, GaSb, GaSe, InAlAsN, InN, InP, InAs, InAsSb, InAsSbP, InGaN, $In_xGa_{1-x}P$, $In_xGa_{1-x}As$, InGaAsN, InGaAsP, InGaAsSb, InGaSb, InMnAs, InSb, TlBr, CdSe, CdS, $Cd_3P_2$, $Cd_3As_2$, $Cd_3Sb_2$, CdTe, CdMnTe, CdZnTe, ZnO, ZnSe, ZnS, ZnTe, $Zn_3P_2$, $ZnSiP_2$, $Zn_3As_2$, $Zn_3Sb_2$, $TiO_2$, $SrTiO_3$, $BaTiO_3$, $VO_2$, $LiNbO_3$, $CrBr_3$, $MoS_2$, FeO, $FeS_2$, NiO, $Cu_2O$, CuO, CuCl, $Cu_2S$, $CuInSe_2$, $Cu(In,Ga)Se_2$, $Cu_2ZnSnS_4$, $Cu_{1.18}Zn_{0.40}Sb_{1.90}S_{7.2}$, $Cu_2SnS_3$, $Ag_2S$, $AgGaS_2$, $Si_{1-x}Ge_x$, $Si_{1-x}Sn_x$, $PbI_2$, PbSe, PbS, PbTe, PbMnTe, $Pb_{1-x}Sn_xTe$, $SnO_2$, SnS, $SnS_2$, SnTe, PbSnTe, $Pb_{1-x}Sn_xTe$, $Tl_2SnTe_5$, $Tl_2GeTe_5$, $As_2S_3$, $As_4S_4$, $Bi_2O_3$, $Bi_2S_3$, $Bi_2Te_3$, $BiI_3$. Preferably the semiconductor material is selected from the group consisting of InGaN (indium gallium nitride)/GaN (gallium nitride), GaP (gallium phosphide), AlGaInP (aluminium gallium indium phosphide), AlGaP (aluminium gallium phosphide), ZnO (zinc oxide).

In a further specified embodiment of the inventive process, the filter-free, electroluminescent lighting device comprises, preferably consists of at least one light emitting diode (LED). Light emitting diodes are cheap in production, provide a distinct light spectrum and deliver small to almost no waste heat, which makes them a very versatilely employable light source in the inventive process. Lighting energy applied to the reaction mixture is to be easily adjusted simply by connecting in series as many light emitting diodes as required for the defined energy input. A further option of adjusting energy input into the reaction mixture is possible with the light emitting diode. By varying the courant and/or voltage applied to said light emitting diode, one changes the brightness of the diode, viz. the luminous flux, thus the energy, entering the reaction mixture. Yet another method of adjusting energy input into the reaction mixture is on controlling the time of irradiation. Since light emitting diodes have a much longer operation or service life compared to mercury vapor lamps or xenon arc lamps viz. xenon discharge lamps, and as such light emitting diodes do not suffer from performance loss accumulating during operation, said light emitting diodes largely reduce costs for conducting the inventive process.

In a preferred embodiment of the inventive process the lighting device comprises, preferably consists of at least one light emitting diode (LED), said light emitting diode comprising as electroluminescent material a compound selected from at least one compound of the group consisting of Si (silicon) $SiO_2$, SiC, hydrogenated amorphous silicon, Ge, mixtures of arsenic, selenium and tellurium, AlBGaN, AlN, AlGaN, AlGaN/AlN, AlGaP, AlGaAs, AlGaAsP, AlInGaP, AlGaInP, GaN, GaAs, GaP, GaAsP, GaInN, GaInP, InN, InP, InGaN, InGaN/AlGaN, ZnO, ZnS doped with Mn, ZnS doped with Cu, ZnSe.

In yet another embodiment adapted to wavelengths in the middle of the visible spectrum, the lighting device comprises, preferably consists of at least one light emitting diode (LED), said light emitting diode comprising as electroluminescent material at least one compound selected from the group consisting of AlGaP, AlGaAsP, AlGaInP, GaN, GaP, GaInP, InGaN, ZnO. Said electroluminescent materials exhibit strong light emission in the middle of the visible spectrum, viz. they emit light ranging from turquoise over green to yellow. The energy of this light is still sufficient for obtaining all-E-retinoid compound of formula 1.

In many embodiments of the inventive process the reaction mixture prior to irradiation is in the form of a homogeneous phase, a supersaturated homogeneous phase or in form of an emulsion or supersaturated emulsion. Supersaturated within this disclosure means, that a compound is diluted in a solvent or solvent mixture to an extent that is close to its solubility product or even has already passed it (colloidal solution), however precipitation does not yet take place. During irradiation the amount of retinoid compound of formula 1 increases up to a point where retinoid compound of formula 1 begins to precipitate in form of crystals. Said crystal formation on one hand is desired. However, with these crystals also some mother liquor is kind of segregated from the reaction mixture and can no longer be homogeneously irradiated. To avoid this in one embodiment of the inventive process, only a distinct portion of the reaction mixture is irradiated. By this operation one part of the reaction mixture remains as is prior to irradiation, whereas another part transforms into a suspension with precipitating crystals.

Irradiating only a distinct portion of the reaction mixture can be realized in two ways. In one embodiment, only a distinct portion of the reaction mixture is irradiated by arranging the filter-free, electroluminescent lighting device emitting monochromatic light such that only a section, i.e. the upper part, the lower part, the left part or the right part of the reaction mixture is exposed to monochromatic light form the filter-free, electroluminescent lighting device. In an embodiment especially adapted to large reaction mixtures, only a distinct portion of the reaction mixture is irradiated by conducting the reaction mixture in a circuit and only exposing a section of said circuit to monochromatic light form the filter-free, electroluminescent lighting device. The circuit is understood to be any arrangement of pipes, tubes, and/or vessels into which the reaction mixture is circulated.

In another embodiment of the inventive process for obtaining an all-E retinoid compound or a mixture of all-E retinoid compounds of formula 1, at least one of the retinoid compounds of formula 2 to 5 or at least one of the retinoid compounds of formula 2 to 5 mixed with compound of formula 1, an organic solvent and a photosensitizer is fed into the reaction device, and the thus obtained reaction mixture, at a temperature ranging from −20° C. to 30° C., is irradiated by means of a filter-free, electroluminescent lighting device emitting monochromatic light, at least 90% of the power of said monochromatic light and at most 100% of said power being emitted in the range from 460 nm to 580 nm.

The given low or moderate temperatures diminish or prevent degradation or damage of retinoid compounds of formula 1 to 5.

Degradation or damage of retinoid compounds of formula 1 to 5 in the inventive process for obtaining an all-E retinoid compound or a mixture of all-E retinoid compounds of formula 1, can be further reduced, provided at least one of the retinoid compounds of formula 2 to 5 or at least one of the retinoid compounds of formula 2 to 5 mixed with compound of formula 1, an organic solvent, a photosensitizer is fed into the reaction device, and the thus obtained reaction mixture, at a temperature ranging from −10° C. to 20° C. is irradiated by means of a filter-free, electroluminescent lighting device emitting monochromatic light, at least 90% of the power of said monochromatic light and at most 100% of said power being emitted in the range from 460 nm to 580 nm.

Increasing temperature in chemical reactions accelerates the reaction rate and consequently also the amount of product formed in a definite time. This, however could not be observed with the inventive process. To the contrary, reaction rate and product yield increased with lowering temperature during the course of the inventive process. It was observed, that reducing the reaction temperature during the feeding and/or during irradiation and/or after irradiation accelerated product formation. An embodiment of the inventive process, aiming to achieve very high product yield thus determines at least one of the retinoid compounds of formula 1 to 5 in an organic solvent supplemented with a photosensitizer to be irradiated at a temperature ranging from −20° C. to 30° C. with lowering the reaction temperature during the course of the reaction, in particular during the course of and/or after irradiation.

The term reaction when related to the inventive process, is understood to comprise at least the feeding and the irradiation step. In the previously mentioned embodiment it comprises the feeding step, the irradiation step and an incubation step, which follows the irradiation step. The incubation step is understood to be a period after irradiation, where the reaction mixture is maintained without irradiation or is cooled down without irradiation.

Provided reaction temperatures are low, e.g., below 10° C. this tends to make the reaction mixture more viscous, thus hampers good intermixing of the reaction mixture. To meet and counter this, in one further embodiment the inventive process for obtaining an all-E retinoid compound or a mixture of all-E retinoid compounds of formula 1

1

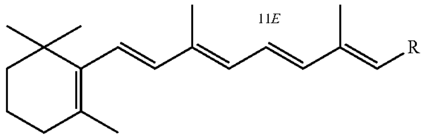

with R being selected from the group of moieties consisting of $CH_2$—OH, CHO, $CH_2$—$OR^2$, COOH, $COOR^3$;

with $R^2$ being (C═0)-alkyl;

with $R^3$ being alkyl;

with alkyl being selected from the group consisting of methyl, ethyl, propyl, isopropyl, butyl, 2-butyl, sec-butyl, isobutyl, tert.-butyl;

comprising the reaction steps:

feeding a retinoid compound of formula 2

2

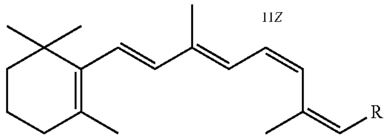

or a retinoid compound of formula 3

3

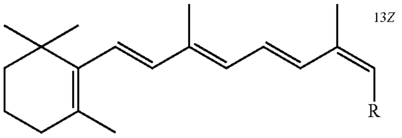

or a retinoid compound of formula 4

4

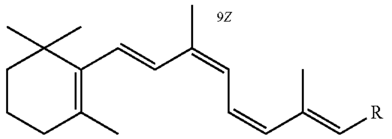

or a retinoid compound of formula 5

5

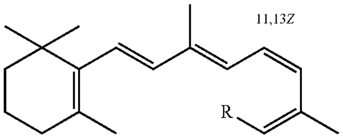

or a mixture of at least two of retinoid compounds 2 to 5, or a mixture of at least one of retinoid compounds 2 to 5 and retinoid compound of formula 1, an organic solvent and a photosensitizer into a reaction device, irradiating the thus obtained reaction mixture by means of a filter-free, electroluminescent lighting device emitting monochromatic light, at least 90% of the power of said monochromatic light and at most 100% of said power being emitted in the range from 460 nm to 580 nm.

defines at least one of the reaction steps being realized under pressure.

High yields in short reaction times are also obtained with a process for obtaining an all-E retinoid compound or a mixture of all-E retinoid compounds of formula 1

1

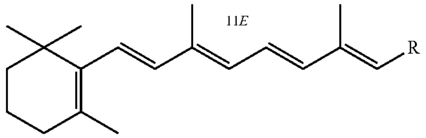

with R being selected from the group of moieties consisting of $CH_2$—OH, CHO, $CH_2$—$OR^2$, COOH, $COOR^3$;

with $R^2$ being (C═0)-alkyl;

with $R^3$ being alkyl;

with alkyl being selected from the group consisting of methyl, ethyl, propyl, isopropyl, butyl, 2-butyl, sec-butyl, isobutyl, tert.-butyl;

comprising the reaction steps:

feeding a retinoid compound of formula 2

2

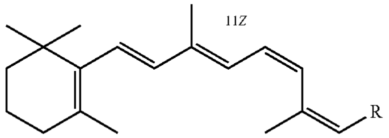

or a retinoid compound of formula 3

3

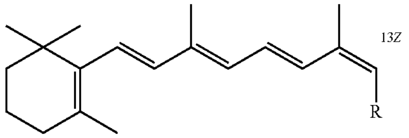

or a retinoid compound of formula 4

4

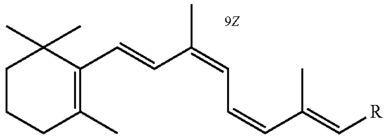

or a retinoid compound of formula 5

5

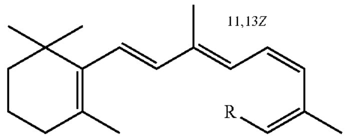

or a mixture of at least two of retinoid compounds 2 to 5, or a mixture of at least one of retinoid compounds 2 to 5 and retinoid compound of formula 1, an organic solvent and a photosensitizer into a reaction device, irradiating the thus obtained reaction mixture at a temperature ranging from −20° C. to 30° C. with lowering the reaction temperature during the course of the reaction, in particular during the course of and/or after irradiation, by means of a filter-free, electroluminescent lighting device emitting monochromatic light, at least 90% of the power of said monochromatic light and at most 100% of said power being emitted in the range from 460 nm to 580 nm, with at least one of the reaction steps being realized under pressure.

Pressure as understood within this disclosure means values ranging from ambient pressure to 100 bar (ambient pressure meaning 1 bar in average depending on climatic and altitude condition without applying any device suited to reduce or increase pressure).

Each of the previously mentioned two embodiments in a further extended version comprises the pressure to range from ambient pressure to 100 bar (ambient pressure meaning 1 bar in average depending on climatic and altitude condition without applying any device suited to reduce or increase pressure).

On the other hand, at higher temperatures viscosity tends to drop. Furthermore, it might be desirable to change the amount of organic solvent during the course of the inventive process, for instance in order to obtain a supersaturated reaction mixture.

This need is addressed in one further embodiment of the inventive process for obtaining an all-E retinoid compound or a mixture of all-E retinoid compounds of formula 1

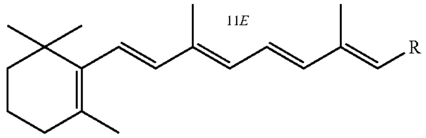
1 with R being selected from the group of moieties consisting of $CH_2$—OH, CHO, $CH_2$—$OR^2$, COOH, $COOR^3$;

with $R^2$ being (C═0)-alkyl;

with $R^3$ being alkyl;

with alkyl being selected from the group consisting of methyl, ethyl, propyl, isopropyl, butyl, 2-butyl, sec-butyl, isobutyl, tert.-butyl;

comprising the reaction steps:

feeding a retinoid compound of formula 2

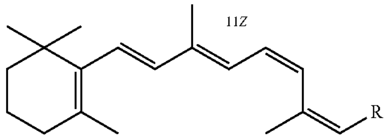
2 or a retinoid compound of formula 3

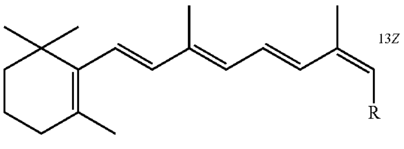
3 or a retinoid compound of formula 4

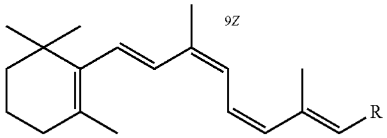
4 or a retinoid compound of formula 5

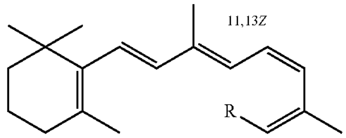
5 or a mixture of at least two of retinoid compounds 2 to 5, or a mixture of at least one of retinoid compounds 2 to 5 and retinoid compound of formula 1, an organic solvent and a photosensitizer into a reaction device, irradiating the thus obtained reaction mixture by means of a filter-free, electroluminescent lighting device emitting monochromatic light, at least 90% of the power of said monochromatic light and at most 100% of said power being emitted in the range from 460 nm to 580 nm.

with at least one of the reaction steps being realized under vacuum.

This previous embodiment can be even further improved and gives higher yields, if it incorporates this additional feature as follows.

Process for obtaining an all-E retinoid compound or a mixture of all-E retinoid compounds of formula 1

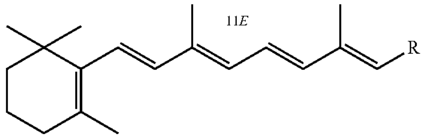
1 with R being selected from the group of moieties consisting of $CH_2$—OH, CHO, $CH_2$—$OR^2$, COOH, $COOR^3$;

with $R^2$ being (C═0)-alkyl;

with $R^3$ being alkyl;

with alkyl being selected from the group consisting of methyl, ethyl, propyl, isopropyl, butyl, 2-butyl, sec-butyl, isobutyl, tert.-butyl;

comprising the reaction steps:

feeding a retinoid compound of formula 2

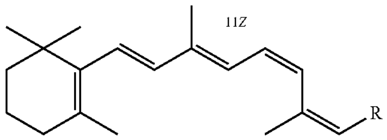
2 or a retinoid compound of formula 3

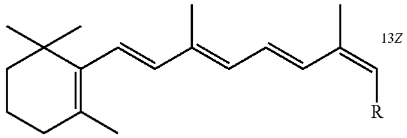

3 or a retinoid compound of formula 4

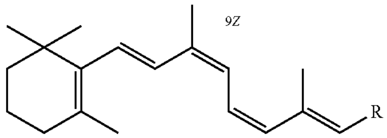

4 or a retinoid compound of formula 5

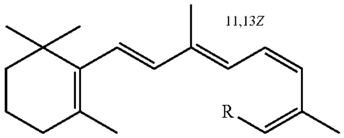

5 or a mixture of at least two of retinoid compounds 2 to 5,
or a mixture of at least one of retinoid compounds 2 to 5 and retinoid compound of formula 1,
an organic solvent and a photosensitizer into a reaction device,
irradiating the thus obtained reaction mixture
at a temperature ranging from −20° C. to 30° C. with lowering the reaction temperature during the course of the reaction, in particular during the course of and/or after irradiation,
by means of a filter-free, electroluminescent lighting device emitting monochromatic light, at least 90% of the power of said monochromatic light and at most 100% of said power being emitted in the range from 460 nm to 580 nm,
with at least one of the reaction steps being realized under vacuum.

Vacuum as disclosed herein means a range from 50 mbar up to ambient pressure (ambient pressure means 1 bar in average as defined supra).

Each of the previously mentioned last two embodiments in a further extended version defines the vacuum to range from 50 mbar to 1 bar.

In order to contribute to the objects 1) of providing a cheap and fast process which provides high selectivities for and high yields of all-E polyunsaturated non-aromatic compound, in particular all-E retinoid compound of formula 1, 2) of avoiding or reducing complicated reaction mixtures and their tedious work-up and 3) in order to ascertain easy up- and downscaling of the inventive process without far-reaching changes in the reaction setup, a further embodiment of the invention determines the following: At least one of the retinoid compounds 1 to 5 is fed in the reaction device such that the overall concentration of at least one of the retinoid compounds 1 to 5 ranges from 5 to 50 w % with respect to the reaction mixture. Preferably at least one of the retinoid compounds 1 to 5 consisting of isomers of retinol acetate is placed in the reaction vessel such that the overall concentration of at least one of the retinoid compounds 1 to 5 ranges from 5 to 50 w % with respect to the reaction mixture. The term "at least one of retinoid compounds 1 to 5" is understood to include respectively one of retinoid compounds 1 to 5, or any permutation of two compounds selected from retinoid compounds 1 to 5 (e.g. 1 and 4; 2 and 3), or any permutation of three compounds selected from retinoid compounds 1 to 5 (e.g. 1 and 2 and 4; 3 and 4 and 5), or any permutation of four compounds selected from retinoid compound 1 to 5, or all 5 retinoid compounds 1 to 5. When using concentrations of retinoid compound, particularly preferred of retinol acetate in the range as previously disclosed, the reaction mixture remains homogenous. No precipitation or formation of complicated reaction mixtures prior to irradiation takes place, which might be the case with higher concentrated reaction mixtures. Reaction mixtures containing less than 5 w % of retinoid compound 1 to 5 would mean manipulating huge amounts of organic solvent thus considerably increasing process costs.

Yet another embodiment defines that the inventive process is realized in a side-loop photoreactor, in a continuous flow-photoreactor or in a submersible photoreactor.

A side loop photoreactor is a reactor introduced in a portion of a reaction circuit or attached to a portion of a reaction circuit. The reaction circuit is an apparatus or a mounting, through which the reaction mixture circulates. Side loop photoreactors can be easily attached or integrated into an existing reaction vessel or reaction plant. From this reaction vessel or reaction plant reaction mixture circulates during operation through the side-loop photoreactor. By doing so, only a portion of the reaction mixture is for a defined time in contact with radiation coming from the filter-free, electroluminescent lighting device (placed in the side-loop photoreactor). Said portion thereafter enters the reaction plant or reaction vessel and again travels through the side-loop photoreactor. By this intermittent contact of reaction mixture with radiation from said lighting device, the course of reaction is accelerated with at the same time further reducing the amount of spoiled or undesired retinoid compounds of formula 2 to 4.

With a continuous flow photoreactor, the reaction mixture only once passes along the electroluminescent lighting device. This type of reactor is favorable if reaction mixtures highly charged with retinoid compound are used or if the power delivered from the electroluminescent lighting device is 800 Wh or nearby with nearby meaning above 500 Wh.

A submersible photoreactor is particularly useful, if one desires to work under pressure or under vacuum, which is easier to realize, when the photoreactor completely immerses into the reaction mixture.

The step "irradiating the thus obtained reaction mixture by means of a filter-free, electroluminescent lighting device emitting monochromatic light, with at least 90% of the power of said monochromatic light and at most 100% of said power being emitted in the range from 460 nm to 580 nm" within this disclosure is also called the photoisomerization step.

The photoisomerization step in one embodiment is followed by crystallization of all-E retinoid compound of formula 1, in particular by crystallization of all-E retinoid compound of formula 1 with R being $CH_2$—O—(C═O)-alkyl and alkyl being selected from the group of methyl, ethyl. Said subsequent crystallization step, e.g. is to be triggered by evaporating of a certain amount of organic solvent.

In a further embodiment, the photoisomerization step and crystallization of all-E retinoid compound of formula 1, in particular crystallization of all-E retinoid compound of formula 1 with R being $CH_2$—O—(C═O)-alkyl and alkyl being selected from the group of methyl, ethyl, are to be performed simultaneously. Said embodiment is preferred. It takes place, when the reaction mixture prior to irradiation is a supersaturated solution/a dispersion and/or when the mixture of at least one representative of the group of C1-C6-alcohols and at least one C5-C10 hydrocarbon is selected such that it forms a uniform phase. In said preferred embodiment, the reaction conditions for obtaining an all-E retinoid compound or a mixture of all-E retinoid compounds of formula 1 are as follows: Feeding a retinoid compound of formula 2, 3, 4 or 5, or a mixture of at least two of retinoid compounds 2 to 5, or a mixture of at least one of retinoid compounds 2 to 5 and retinoid compound of formula 1, an organic solvent and a photosensitizer into a reaction device (preferably in dispersed form), irradiating the thus obtained reaction mixture at 15° C. by means of a filter-free, electroluminescent lighting device emitting monochromatic light, at least 90% of the power of said monochromatic light and at most 100% of said power being emitted in the range from 460 nm to 580 nm, followed by cooling the reaction mixture to a temperature ranging from −10° C. to −15° C. and filtration and washing of the filtercake.

This embodiment when expressed in claim language, reads: Process for obtaining an all-E retinoid compound or a mixture of all-E retinoid compounds of formula 1

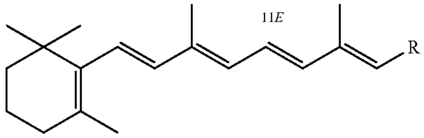

1 with R being selected from the group of moieties consisting of $CH_2$—OH, CHO, $CH_2$—$OR^2$, COOH, $COOR^3$;

with $R^2$ being (C═0)-alkyl;

with $R^3$ being alkyl;

with alkyl being selected from the group consisting of methyl, ethyl, propyl, isopropyl, butyl, 2-butyl, sec-butyl, isobutyl, tert.-butyl;

comprising the reaction steps:

feeding a retinoid compound of formula 2

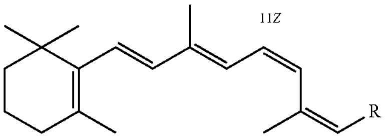

2 or a retinoid compound of formula 3

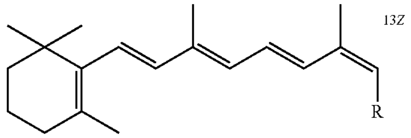

3 or a retinoid compound of formula 4

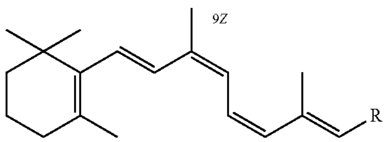

4 or a retinoid compound of formula 5

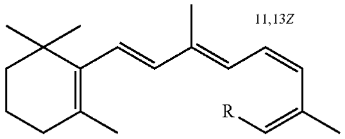

5 or a mixture of at least two of retinoid compounds 2 to 5, or a mixture of at least one of retinoid compounds 2 to 5 and retinoid compound of formula 1, an organic solvent and a photosensitizer into a reaction device, irradiating the thus obtained reaction mixture by means of a filter-free, electroluminescent lighting device emitting monochromatic light, at least 90% of the power of said monochromatic light and at most 100% of said power being emitted in the range from 460 nm to 580 nm;

the organic solvent being a mixture of at least one representative of the group of C1-C6-alcohols and at least one C5-C10 hydrocarbon, said mixture of at least one representative of the group of C1-C6-alcohols and at least one C5-C10 hydrocarbon being selected such that it forms a uniform phase and/or the reaction mixture prior to irradiation being a supersaturated solution/emulsion.

The reaction steps "feeding at least one retinoid compound of formula 1 to 5, an organic solvent, and a photosensitizer", "irradiating the thus obtained reaction mixture" as mentioned in the embodiments supra and the resulting "crystallization of all-E retinoid compound of formula 1" can be carried out in a batch reactor, where the irradiation source is preferably either submerged in the reaction mixture or placed within a side loop of the reactor through which the reaction mixture is circulated. Alternatively, the reaction steps can be carried out semi-continuously, e.g. in cascaded reaction vessels, or continuously, e.g. in a flow reactor.

A yet further elaborated embodiment makes it possible to still increase reaction rate and/or yield of the inventive process. Said embodiment is a process for obtaining an all-E retinoid compound or a mixture of all-E retinoid compounds of formula 1

1

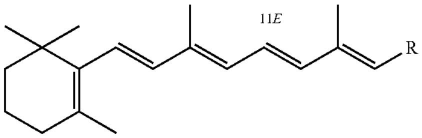

with R being selected from the group of moieties consisting of $CH_2$—OH, CHO, $CH_2$—$OR^2$, COOH, $COOR^3$;

with $R^2$ being (C═0)-alkyl;

with $R^3$ being alkyl;

with alkyl being selected from the group consisting of methyl, ethyl, propyl, isopropyl, butyl, 2-butyl, sec-butyl, isobutyl, tert.-butyl;

comprising the reaction steps:

feeding a retinoid compound of formula 2

2

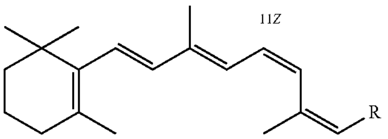

or a retinoid compound of formula 3

3

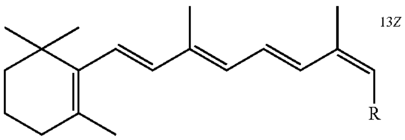

or a retinoid compound of formula 4

4

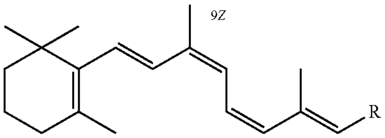

or a retinoid compound of formula 5

5

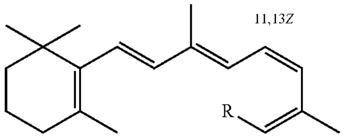

or a mixture of at least two of retinoid compounds 2 to 5, or a mixture of at least one of retinoid compounds 2 to 5 and retinoid compound of formula 1, an organic solvent and a photosensitizer into a reaction device, irradiating the thus obtained reaction mixture by means of a filter-free, electroluminescent lighting device emitting monochromatic light, at least 90% of the power of said monochromatic light and at most 100% of said power being emitted in the range from 460 nm to 580 nm.

and feeding the reaction mixture with at least one seed crystal of compound 1 prior or during irradiation.

The yet further elaborated embodiment mentioned supra is further improved, when the organic solvent used is a mixture of at least one representative of the group of C1-C6-alcohols and at least one C5-C10 hydrocarbon.

Still another advance for this yet further elaborated embodiment is achieved, when the organic solvent used is a mixture of at least one representative of the group of C1-C6-alcohols and at least one C5-C10 hydrocarbon and when said mixture of at least one representative of the group of C1-C6-alcohols and at least one C5-C10 hydrocarbon is selected such that it forms a uniform phase.

Very high yields in short reaction times are obtained with this yet further elaborated embodiment, when the organic solvent used is a mixture of at least one representative of the group of C1-C6-alcohols and at least one C5-C10 hydrocarbon, said mixture of at least one representative of the group of C1-C6-alcohols and at least one C5-C10 hydrocarbon is selected such that it forms a uniform phase and said mixture of at least one representative of the group of C1-C6-alcohols and at least one C5-C10 hydrocarbon comprises methanol or ethanol as C1-C6-alcohol and between 0.1 and 12 w % of a hydrocarbon.

Still further improved yields in short reaction times are obtained with this yet further elaborated embodiment, when the organic solvent used is a mixture of at least one representative of the group of C1-C6-alcohols and at least one C5-C10 hydrocarbon, said mixture of at least one representative of the group of C1-C6-alcohols and at least one C5-C10 hydrocarbon is selected such that it forms a uniform phase and said mixture of at least one representative of the group of C1-C6-alcohols and at least one C5-C10 hydrocarbon comprises methanol as C1-C6-alcohol and between 0.1 and 12 w % of a hydrocarbon, The very high yields in short reaction times are further improved with this yet further elaborated embodiment, when the organic solvent used is a mixture of at least one representative of the group of C1-C6-alcohols and at least one C5-C10 hydrocarbon, said mixture of at least one representative of the group of C1-C6-alcohols and at least one C5-C10 hydrocarbon is selected such that it forms a uniform phase and the mixture of at least one representative of the group of C1-C6-alcohols and at least one C5-C10 hydrocarbon comprises methanol as C1-C6-alcohol and between 1 and 12 w % of heptane including 10 w % and mostly preferred between 1 and 5 w % of heptane.

Yet another embodiment of the invention is the use of the inventive process as disclosed in any one of the previously described embodiments for isomerizing polyunsaturated compounds, in particular for isomerizing polyunsaturated non-aromatic compounds.

The invention and its advantageous features will now be further explained in the specific description including the examples and making reference to the figures.

FIG. 1 Output profile of a xenon arc lamp

FIG. 2 Transmittancy of a $K_2CrO_4$-solution

Figure 3:
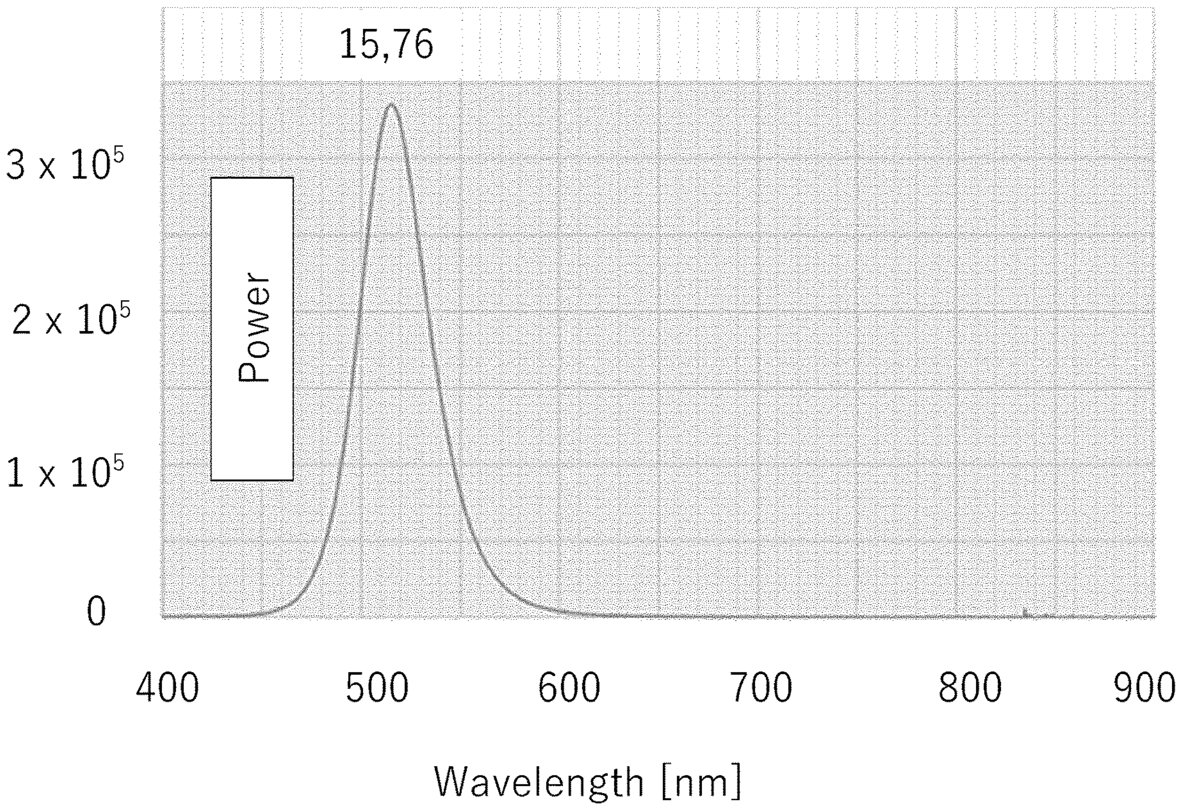

FIG. 3 Emission spectrum of the light emitting diode within the lighting device used Some of the advantageous features of the inventive process are:

1. The yield of all-E retinoid compound of formula 1, viz. all-E retinol acetate is higher when using light emitting diodes (LED's) compared to experiments with conventional high pressure mercury vapour lamps in combination with a chromate filter.

2. There are considerable savings of electric energy for the same amount of all-E retinoid compound of formula 1, in particular of all-E retinol acetate produced.
3. There is a remarkable increase in selectivity. In course of the reaction a considerably reduced amount of retinoid compounds of formula 2 to 5, in particular of 11,13Z-retinol acetate, of 9Z-retinol acetate, and 13Z-retinol acetate are formed with the inventive filter-free, electroluminescent lighting device compared to the high pressure mercury vapor lamp.

FIG. 3 discloses the emission spectrum of the type of light emitting diode (LED) as used in the examples, which are embodiments of the inventive process. One realizes that 90% or more of the emitted light has a wavelength ranging from 460 nm to 580 nm. The power in μW/nm reaching the reaction mixture is adapted to be narrowed further either by changing the angle and/or distance of incident light, i.e. the angle/distance between the light emitting diode and the reaction mixture or by adjusting the voltage/courant applied onto the light emitting diode, or by adjusting the time, the reaction is exposed to light from the electroluminescent lighting device. In a further embodiment power is adjusted or narrowed by the number of light emitting diodes (LED's) used. The electric power consumption per light emitting diode is 2.8 W. Part or all of these adjusting measures can also be combined.

Examples 1 TO 3 and Comparative Example C4

In a 2.5l reaction vessel, equipped with a side-loop photoreactor with either a LED-lamp as electroluminescent lighting device emitting monochromatic light, said LED-lamp comprising a number of light emitting diodes (LED's) as specified in table 1 below, or with a high pressure mercury vapor lamp TQ 150 Z2, are placed 1.049 g of crude vitamin A (containing 941 g 11,13Z-, 9Z-, 13Z-,11Z- and all-E retinol acetate isomers), 1.159 g of methanol, 52 g of heptane and 72 mg erythrosine. At 15° C. the reaction mixture is pumped through the side loop photoreactor and irradiated for 4 h. Samples were taken frequently and subjected to quantitative HPLC. After irradiation, the suspension formed is cooled down to −10° C. and filtered. The filter cake is washed with 500 ml of methanol and dried in a current of nitrogen. The apparatus is rinsed with acetone to collect remaining product. The filter cake, the mother liquor and the acetone rinse are subjected to quantitative HPLC. The sum of amounts of all-E retinol acetate formed in course of the reaction are calculated based on the weight of the filter cakes, mother liquors and acetone rinses, each having a respective all-E retinoid amount as determined by HPLC w %. The yields are calculated based on the total amount of retinol acetate isomers subjected into the reaction.

Table 1: Total amount of all-E retinol acetate and yield obtained in examples 1-3 and comparative example C4. All experiments were performed with the same starting material and the same photoreactor.

TABLE 1

| Example | Total mass of all E retionol acetate in crude vitamin A prior to irradiaton [g] | Number of LEDs/ mercury lamp applied | Total mass of all-E retinol acetate [g] | Yield [%] |
|---|---|---|---|---|
| 1 | 533.7 | 48 | 722.5 | 76.8 |
| 2 | 533.7 | 36 | 699.8 | 74.4 |
| 3 | 533.7 | 24 | 710.2 | 75.5 |
| C4 | 533.7 | TQ 150 Z2 + filter | 681.3 | 72.4 |

From Table 1, two things can be noticed. The yield when working with light emitting diodes (LED's) in each of examples 1 to 3 is higher than in comparative example C4 using the high pressure mercury vapor lamp. The highest yield of all-E retinol acetate can be obtained with the highest amount of light emitting diodes (LED's) used. However, also with a reduced amount of light emitting diodes (cf. example 3) increased yields can be obtained.

Example 1 to 3 and Comparative Example C4 (Energy Consumption)

Table 2 discloses the electric energy spent for making 1 kg of all-E retinol acetate of example 1-3 and of comparative example C4. The electric power consumption per light emitting diode (LED) amounts to 2.8 W and for the mercury lamp TQ 150 Z2 it amounts to 150 W.

TABLE 2

| Example | Total mass of all E retionol acetate prior to irradiaton [g] | Number of LEDs/ mercury lamp applied | Total mass (all-E retinol acetate) [g] | Electric energy [Wh] | Electric energy/all-E retinol acetate [Wh/kg] |
|---|---|---|---|---|---|
| 1 | 533.7 | 48 | 722.5 | 537.6 | 744.1 |
| 2 | 533.7 | 36 | 699.8 | 403.2 | 576.2 |
| 3 | 533.7 | 24 | 710.2 | 268.8 | 378.5 |
| C4 | 533.7 | TQ 150 Z2 + filter | 681.3 | 600.0 | 880.7 |

The amount of electric energy (Wh) employed is calculated as follows: Number of light emitting diodes×power per light emitting diode×time of exposure. Regarding for instance example 1, this is 48×2.8 W×4 h=537.6 Wh. Said amount of electric energy in column 6 of table 2 is related to 1 kg of all-E retinol acetate produced.

One observes in table 2, that the high pressure mercury vapor lamp requires more electric energy for producing 1 kg of all-E retinol acetate than the light emitting diodes (LED's) used. The consumption of electric energy by the light emitting diodes (LED's) increases with the number of LED's used.

Example 1 to 3 and Comparative Example C4 (Formation of Undesired Isomers of Retinol Acetate)

Table 3 discloses the concentration of undesired 11,13Z—, 9Z-, 13Z-isomers of retinol acetate in the reaction mixture prior to irradiation and formed in course of the reaction in examples 1-3 and comparative example C4. It further discloses in examples 1-3 and comparative example C4 the concentration of the sum of Z-isomers of retinol acetate present in the reaction mixture prior to irradiation and formed after four hours of irradiation.

TABLE 3

| | Example | | | | | | | |
|---|---|---|---|---|---|---|---|---|
| | 1 | | 2 | | 3 | | C4 | |
| Reaction time (h) | Sum (11,13Z-, 9Z-, 13Z-retinol acetate) (w %) | Sum of Z-isomers in crude vitamin A (w %) | Sum (11,13Z-, 9Z-, 13Z-retinol acetate) (w %) | Sum of Z-isomers in crude vitamin A (w %) | Sum (11,13Z-, 9Z-, 13Z-retinol acetate) (w %) | Sum of Z-isomers in crude vitamin A (w %) | Sum (11,13Z-, 9Z-, 13Z-retinol acetate) (w %) | Sum of Z-isomers in crude vitamin A (w %) |
| 0.00 | 13.49 | 38.8 | 13.49 | 38.8 | 13.49 | 38.8 | 13.49 | 38.8 |
| 0.50 | 14.63 | — | 14.47 | — | 14.79 | — | 16.40 | — |
| 1.00 | 15.55 | — | 15.08 | — | 15.97 | — | 16.72 | — |
| 2.00 | 15.14 | — | 15.09 | — | 15.83 | — | 16.94 | — |
| 3.00 | 14.14 | — | 14.54 | — | 15.23 | — | 16.37 | — |
| 4.00 | 13.96 | 16.2 | 14.04 | 17.5 | 15.46 | 18.5 | 16.00 | 19.6 |

From table 3, it can be seen that the amount of undesired so-called Z-isomers of retinol acetate is the highest prior to irradiation. It decreases during the course of irradiation and it is always the highest, when using the high pressure mercury vapor lamp. With 24 LED's (example 3), 36 LED's (example 2) and 48 LED's (example 1) the amount of undesired isomers is always inferior to this one obtained with the high pressure mercury vapor lamp. The lowest amount of undesired isomers is obtained when one uses 48 LED's during a time of 3 to 4 h (cf. example 1).

One learns from this disclosure about an improved process for isomerizing polyunsaturated non-aromatic compounds including acyclic conjugated polyenes and alicyclic conjugated polyenes. In particular it is an improved and safe process for forming all-E retinoid compounds in high yield by expending as few energy as possible and with avoiding at most possible side products or product mixtures. This is achieved by feeding at least one of retinoid compounds of formula 2 to 5, or at least one of retinoid compounds of formula 2 to 5 and retinoid compound of formula 1, an organic solvent and a photosensitizer into a reaction device and irradiating the thus obtained reaction mixture with visible monochromatic light, at least 90% of the power of said monochromatic light and at most 100% of said power being emitted in the range from 460 nm to 580 nm. Good results are obtained, when the reaction mixture comprises an organic solvent, being a mixture of at least two solvents and the electroluminescent lighting device used is a semiconductor material. Using the inventive process for isomerizing polyunsaturated compounds, in particular for isomerizing polyunsaturated non-aromatic compounds is another crucial topic of the invention.

The invention claimed is:

1. Process for obtaining an all-E retinoid compound or a mixture of all-E retinoid compounds of formula 1

1

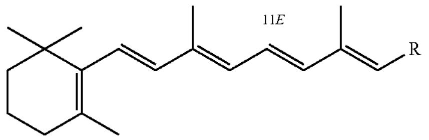

with R being selected from the group of moieties consisting of $CH_2$—OH, CHO, $CH_2$—$OR^2$, COOH, $COOR^3$, with $R^2$ being (C═O)-alkyl, with $R^3$ being alkyl;

with alkyl being selected from the group consisting of methyl, ethyl, propyl, isopropyl, butyl, 2-butyl, sec-butyl, isobutyl, tert-butyl;

comprising the reaction steps:

feeding a retinoid compound of formula 2

2

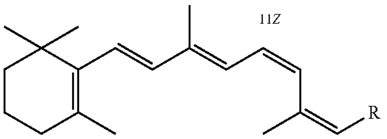

or a retinoid compound of formula 3

3

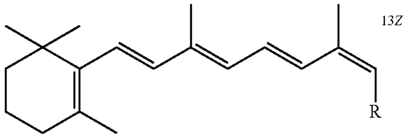

or a retinoid compound of formula 4

4

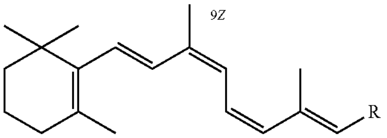

or a retinoid compound of formula 5

5

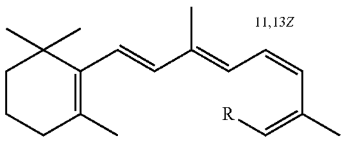

or a mixture of at least two of retinoid compounds 2 to 5, or a mixture of at least one of retinoid compounds 2 to 5 and retinoid compound of formula 1, an organic solvent and a photosensitizer into a reaction device, irradiating the thus obtained reaction mixture by means of a filter-free, electroluminescent lighting device emitting monochromatic light, at least 90% of the power of said monochromatic light and at most 100% of said power being emitted in the range from 460 nm to 580 nm;

wherein only a distinct portion of the reaction mixture is irradiated.

2. Process according to claim 1, wherein at least 90% of the power of said monochromatic light and at most 100% of said power being emitted in the range from 501 nm to 550 nm.

3. Process according to claim 1, wherein the monochromatic light is selected such that the electric energy consumed by said lighting device for obtaining 1 kg of retinoid compound of formula 1 does not exceed 800 Wh.

4. The process according to claim 1, wherein R is $CH_2$—O—(C═O)— alkyl with alkyl being selected from the group of methyl, ethyl.

5. The process according to claim 1, wherein the weight portion of the sum of retinoid compound of formula 1 and formula 2 prior to irradiation amounts to at least 80 w % of the retinoid compounds present in the reaction mixture, said retinoid compounds being selected from the group of retinoid compound of formula 1, retinoid compound of formula 2, retinoid compound of formula 3, retinoid compound of formula 4 and retinoid compound of formula 5.

6. The process according to claim 1, wherein the organic solvent is a mixture of at least one representative of the group of C1-C6-alcohols and at least one C5-C10 hydrocarbon.

7. The process according to claim 6, wherein the mixture of at least one representative of the group of C1-C6-alcohols and at least one C5-C10 hydrocarbon is selected such that it forms a uniform phase.

8. The process according to claim 6, wherein the mixture of at least one representative of the group of C1-C6-alcohols and at least one C5-C10 hydrocarbon comprises between 0.1 and 12 w % of a hydrocarbon.

9. The process according to claim 6, wherein the mixture of at least one representative of the group of C1-C6-alcohols and at least one C5-C10 hydrocarbon comprises between 1 and 12 w % of a heptane.

10. The process according to claim 6, wherein the mixture of at least one representative of the group of C1-C6-alcohols and at least one C5-C10 hydrocarbon comprises between 1 and 5 w % of a heptane.

11. The process according to claim 1, wherein the photosensitizer is selected from at least one compound of the group consisting of fluorescein, eosin, rose bengal, erythrosine, cobalt-tetraphenylporphyrin, zinc-tetraphenylporphyrin, rhodamine B, basacryl brilliant red, iodine.

12. The process according to claim 1, wherein the lighting device comprises a semiconductor material.

13. The process according to claim 1, wherein the lighting device comprises at least one light emitting diode (LED).

14. The process according to claim 1, wherein at least one of the retinoid compounds of claim 1 is irradiated at a temperature ranging from −20° C. to 30° C. with lowering the reaction temperature during the course of the reaction.

15. The process according to claim 1, wherein at least one of the retinoid compounds 1 to 5 is fed in the reaction device such that the overall concentration of at least one of the retinoid compounds 1 to 5 ranges from 5 to 50 w % with respect to the reaction mixture.

16. The process according to claim 1, wherein at least one of the retinoid compounds 1 to 5 is fed in the reaction device such that the overall concentration of at least one of the retinoid compounds 1 to 5 ranges from 5 to 50 w % with respect to the reaction mixture.

17. The process according to claim 1, wherein the process is realized in a side-loop photoreactor, in a continuous flow-photoreactor or in a submersible photoreactor.

18. The process according to claim 16, wherein the at least one of the retinoid compounds 1 to 5 consists of isomers of retinol acetate.

19. The process according to claim 12, wherein the semiconductor material is selected from the group consisting of silicon, diamond, germanium, α-tin, α-sulfur, selenium, tellurium, BN, BP, BAs, $B_{12}As_2$, AlN, AlP, AlAs, AlGaN, AlGaP, $Al_xGa_{1-x}As$, AlGaAsN, AlGaAsP, AlGaInP, $Al_xIn_{1-x}As$, AlInAsP, AlSb, $Al_xIn_{1-x}Sb$, GaN, GaAsN, GaP, GaAs, GaAsP, GaAsSb, GaAsSbN, GaAsSbN, GaInAsSbP, GaMnAs, GaSb, GaSe, InAlAsN, InN, InP, InAs, InAsSb, InAsSbP, InGaN, $In_xGa_{1-x}P$, $In_xGa_{1-x}As$, InGaAsN, InGaAsP, InGaAsSb, InGaSb, InMnAs, InSb, TIBr, CdSe, CdS, $Cd_3P_2$, $Cd_3As_2$, $Cd_3Sb_2$, CdTe, CdMnTe, CdZnTe, ZnO, ZnSe, ZnS, ZnTe, $Zn_3P_2$, $ZnSiP_2$, $Zn_3As_2$, $Zn_3Sb_2$, $TiO_2$, $SrTiO_3$, $BaTiO_3$, $VO_2$, $LiNbO_3$, $CrBr_3$, $MoS_2$, FeO, $FeS_2$, NiO, $Cu_2O$, CuO, CuCl, $Cu_2S$, $CuInSe_2$, $Cu(In,Ga)Se_2$, $Cu_2ZnSnS_4$, $Cu_{1.18}Zn_{0.40}$ $Sb_{1.90}S_{7.2}$, $Cu_2SnS_3$, $Ag_2S$, $AgGaS_2$, $Si_{1-x}Ge_x$, $Si_{1-x}Sn_x$, $PbI_2$, PbSe, PbS, PbTe, PbMnTe, $Pb_{1-x}Sn_xTe$, $SnO_2$, SnS, $SnS_2$, SnTe, PbSnTe, $Pb_{1-x}Sn_xTe$, $Tl_2SnTe_5$, $Tl_2GeTe_5$, $As_2S_3$, $As_4S_4$, $Bi_2O_3$, $Bi_2S_3$, $Bi_2Te_3$, and $BiI_3$.

20. The process according to claim 12, wherein the semiconductor material is selected from the group consisting of InGaN/GaN, AlGaInP, AlGaP, and ZnO.

21. The process according to claim 1, wherein the lighting device comprises at least one light emitting diode (LED) comprising as electroluminescent material a compound selected from the group consisting of Si, $SiO_2$, SiC, hydrogenated amorphous silicon, Ge, mixtures of arsenic, selenium and tellurium, AlBGaN, AlN, AlGaN, AlGaN/AlN, AlGaP, AlGaAs, AlGaAsP, AlInGaP, AlGaInP, GaN, GaAs, GaP, GaAsP, GaInN, GaInP, InN, InP, InGaN, InGaN/AlGaN, ZnO, ZnS doped with Mn, ZnS doped with Cu, and ZnSe.

22. The process according to claim 1, wherein at least 90% of the power of said monochromatic light and at most 100% of said power being emitted in the range from 501 nm to 550 nm.

* * * * *